(12) United States Patent
Trombley, III et al.

(10) Patent No.: US 9,764,081 B2
(45) Date of Patent: Sep. 19, 2017

(54) FLUID PATH CONTAINING A PRESSURE ISOLATION VALVE

(71) Applicant: Bayer HealthCare LLC, Whippany, NJ (US)

(72) Inventors: Frederick W. Trombley, III, Gibsonia, PA (US); David M. Reilly, Glenshaw, PA (US); Alan D. Hirschman, Glenshaw, PA (US); David M. Griffiths, Pittsburgh, PA (US); Gerald W. Callan, Greensburg, PA (US); Luis A. Pedraza, West Roxbury, MA (US); Jennie Kwo, Cambridge, MA (US); Christopher T. Zirps, Sharon, MA (US); Roderick H. Beaulieu, Cumberland, RI (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 522 days.

(21) Appl. No.: 14/272,725

(22) Filed: May 8, 2014

(65) Prior Publication Data

US 2014/0249485 A1    Sep. 4, 2014

Related U.S. Application Data

(62) Division of application No. 11/238,666, filed on Sep. 29, 2005, now Pat. No. 8,747,358, which is a division
(Continued)

(51) Int. Cl.
*A61M 5/00* (2006.01)
*A61M 5/145* (2006.01)
(Continued)

(52) U.S. Cl.
CPC ........ *A61M 5/007* (2013.01); *A61M 5/14546* (2013.01); *A61M 31/005* (2013.01);
(Continued)

(58) Field of Classification Search
CPC .............. A61M 5/007; A61M 5/14546; A61M 5/16827; A61M 31/005; A61M 39/22;
(Continued)

(56) References Cited

U.S. PATENT DOCUMENTS 2,335,085 A    11/1943  Roberts
2,485,842 A    10/1949  Pennington
(Continued)

FOREIGN PATENT DOCUMENTS

CA    2045070 A1    2/1992
EP    1172124 A2    1/2002
(Continued)

*Primary Examiner* — Kami A Bosworth
(74) *Attorney, Agent, or Firm* — Joseph L. Kent; David Schramm; James R. Stevenson

(57) ABSTRACT

A fluid path set including a multi-patient use section adapted for connection with a pump device and a source of injection fluid, and a per-patient use section adapted for removable fluid communication with the multi-patient use section. The per-patient use section includes a pressure isolation mechanism having a first port adapted for connection to the pump device via the multi-patient use section, a second port adapted for connection to a patient, and a pressure isolation port adapted for connection to a source of medical fluid via the multi-patient use section. The per-patient use section includes a valve member biased to a normally open position permitting fluid communication between the first port, the second port, and the pressure isolation port, and movable to a closed position to close the pressure isolation port when
(Continued)

fluid pressure reaches a predetermined pressure level sufficient to overcome a biasing force applied to the valve member.

20 Claims, 9 Drawing Sheets

Related U.S. Application Data of application No. 09/982,518, filed on Oct. 18, 2001, now Pat. No. 7,094,216.

(60) Provisional application No. 60/241,505, filed on Oct. 18, 2000.

(51) Int. Cl.
*A61M 31/00* (2006.01)
*A61M 39/22* (2006.01)
*A61M 5/168* (2006.01)
*A61M 5/14* (2006.01)

(52) U.S. Cl.
CPC ......... *A61M 39/22* (2013.01); *A61M 5/16827* (2013.01); *A61M 2005/1403* (2013.01); *A61M 2205/582* (2013.01); *A61M 2209/01* (2013.01); *Y10T 137/7727* (2015.04)

(58) Field of Classification Search
CPC ........ A61M 39/225; A61M 2005/1403; A61M 2209/01; Y10T 137/7722; Y10T 137/7723; Y10T 137/7726; Y10T 137/7727; Y10T 137/7728; Y10T 137/7729
See application file for complete search history.

(56) References Cited

U.S. PATENT DOCUMENTS

| | | | |
|---|---|---|---|
| 2,590,838 A | 4/1952 | Boggs |
| 2,702,547 A | 2/1955 | Glass |
| 2,985,192 A | 5/1961 | Roberts et al. |
| 3,017,881 A | 1/1962 | Smith |
| 3,057,350 A | 10/1962 | Cowley |
| 3,157,201 A | 11/1964 | David |
| 3,411,534 A | 11/1968 | Rose |
| 3,450,152 A | 6/1969 | Ouellette |
| 3,701,345 A | 10/1972 | Heilman et al. |
| 3,834,372 A | 9/1974 | Turney |
| 3,865,134 A | 2/1975 | Holcomb |
| 3,918,490 A | 11/1975 | Goda |
| 3,935,971 A | 2/1976 | Papoff et al. |
| 3,957,082 A | 5/1976 | Fuson et al. |
| 4,061,142 A | 12/1977 | Tuttle |
| 4,071,039 A | 1/1978 | Goof |
| 4,080,967 A | 3/1978 | O'Leary |
| 4,094,318 A | 6/1978 | Burke et al. |
| 4,121,622 A | 10/1978 | Forberg |
| 4,230,151 A | 10/1980 | Jonsson |
| 4,243,031 A | 1/1981 | Genese |
| 4,246,452 A | 1/1981 | Chandler |
| 4,259,985 A | 4/1981 | Bergmann |
| 4,328,834 A | 5/1982 | Oates et al. |
| 4,351,332 A | 9/1982 | Whitney et al. |
| 4,370,982 A | 2/1983 | Reilly |
| 4,396,385 A | 8/1983 | Kelly et al. |
| 4,459,036 A | 7/1984 | Sado et al. |
| 4,464,172 A | 8/1984 | Lichtenstein |
| 4,468,914 A | 9/1984 | Pestes |
| 4,484,599 A | 11/1984 | Hanover et al. |
| 4,491,156 A | 1/1985 | Lee, II |
| 4,559,036 A | 12/1985 | Wunsch |
| 4,637,817 A | 1/1987 | Archibald et al. |
| 4,677,980 A | 7/1987 | Reilly et al. |
| 4,684,102 A | 8/1987 | Dykstra |
| 4,710,166 A | 12/1987 | Thompson et al. |
| 4,819,637 A | 4/1989 | Dormandy, Jr. et al. |
| 4,821,996 A | 4/1989 | Bellotti et al. |
| 4,838,856 A | 6/1989 | Mulreany et al. |
| 4,854,324 A | 8/1989 | Hirschman et al. |
| 4,858,127 A | 8/1989 | Kron et al. |
| 4,925,444 A | 5/1990 | Orkin et al. |
| 4,946,434 A | 8/1990 | Plaisted et al. |
| 4,967,797 A | 11/1990 | Manska |
| 4,993,546 A | 2/1991 | Southard |
| 5,002,528 A | 3/1991 | Palestrant |
| 5,007,904 A | 4/1991 | Densmore et al. |
| 5,021,046 A | 6/1991 | Wallace |
| 5,057,081 A | 10/1991 | Sunderland et al. |
| 5,084,031 A | 1/1992 | Todd et al. |
| 5,097,840 A | 3/1992 | Wallace et al. |
| 5,104,387 A | 4/1992 | Pokorney et al. |
| 5,106,379 A | 4/1992 | Leap |
| 5,113,906 A | 5/1992 | Hogner |
| 5,117,870 A | 6/1992 | Goodale et al. |
| 5,135,026 A | 8/1992 | Manska |
| 5,143,257 A | 9/1992 | Austin et al. |
| 5,152,776 A | 10/1992 | Pinchuk |
| 5,190,071 A | 3/1993 | Sule |
| 5,199,604 A | 4/1993 | Palmer et al. |
| 5,205,322 A | 4/1993 | Merick et al. |
| 5,207,642 A | 5/1993 | Orkin et al. |
| 5,259,985 A | 11/1993 | Nakanishi et al. |
| 5,273,537 A | 12/1993 | Haskvitz et al. |
| 5,300,031 A | 4/1994 | Neer et al. |
| 5,336,051 A | 8/1994 | Tamari |
| 5,356,375 A | 10/1994 | Higley |
| 5,377,718 A | 1/1995 | Sand |
| 5,383,858 A | 1/1995 | Reilly et al. |
| 5,429,611 A | 7/1995 | Rait |
| 5,433,712 A | 7/1995 | Stiles et al. |
| 5,450,847 A | 9/1995 | Kampfe et al. |
| 5,460,609 A | 10/1995 | O'Donnell |
| 5,462,251 A | 10/1995 | Kawabe |
| 5,515,851 A | 5/1996 | Goldstein |
| 5,569,208 A | 10/1996 | Woelpper et al. |
| 5,573,505 A | 11/1996 | Johnson et al. |
| 5,573,515 A | 11/1996 | Wilson et al. |
| 5,584,671 A | 12/1996 | Schweitzer, Jr. et al. |
| 5,592,940 A | 1/1997 | Kampfe et al. |
| 5,593,385 A * | 1/1997 | Harrison ............ A61M 5/1412 604/83 |
| 5,672,155 A | 9/1997 | Riley et al. |
| 5,730,418 A | 3/1998 | Feith et al. |
| 5,770,675 A | 6/1998 | Kim et al. |
| 5,779,675 A | 7/1998 | Reilly et al. |
| 5,800,397 A | 9/1998 | Wilson et al. |
| 5,806,519 A | 9/1998 | Evans, III et al. |
| 5,807,349 A | 9/1998 | Person et al. |
| 5,817,068 A | 10/1998 | Urrutia |
| 5,840,026 A | 11/1998 | Uber, III et al. |
| 5,865,797 A | 2/1999 | Zeeman |
| 5,873,861 A | 2/1999 | Hitchins et al. |
| 5,882,343 A | 3/1999 | Wilson et al. |
| 5,885,216 A | 3/1999 | Evans, III et al. |
| 5,901,745 A | 5/1999 | Buchtel |
| 5,916,165 A | 6/1999 | Duchon et al. |
| 5,916,197 A | 6/1999 | Reilly et al. |
| 5,938,639 A | 8/1999 | Reilly et al. |
| 5,947,935 A | 9/1999 | Rhinehart et al. |
| 5,961,488 A * | 10/1999 | Barak ............... A61M 5/16827 604/246 |
| 5,988,587 A | 11/1999 | Duchon et al. |
| 6,079,691 A | 6/2000 | Dragone |
| 6,096,011 A | 8/2000 | Trombley, III et al. |
| 6,099,502 A | 8/2000 | Duchon et al. |
| 6,099,511 A * | 8/2000 | Devos ................ A61M 5/1408 604/246 |
| 6,197,000 B1 | 3/2001 | Reilly et al. |
| 6,221,045 B1 | 4/2001 | Duchon et al. |
| 6,293,958 B1 | 9/2001 | Berry et al. |
| 6,306,117 B1 | 10/2001 | Uber, III |
| 6,336,913 B1 | 1/2002 | Spohn et al. |

(56) References Cited

U.S. PATENT DOCUMENTS

| | | |
|---|---|---|
| 6,339,718 B1 | 1/2002 | Zatezalo et al. |
| 6,344,030 B1 | 2/2002 | Duchon et al. |
| 6,361,528 B1 | 3/2002 | Wilson et al. |
| 6,442,418 B1 | 8/2002 | Evans, III et al. |
| 6,447,481 B1 | 9/2002 | Duchon et al. |
| 6,471,674 B1 | 10/2002 | Emig et al. |
| 6,475,192 B1 | 11/2002 | Reilly et al. |
| RE38,074 E | 4/2003 | Recinella et al. |
| 6,575,930 B1 | 6/2003 | Trombley, III et al. |
| 6,626,862 B1 | 9/2003 | Duchon et al. |
| 6,638,263 B1 | 10/2003 | Theeuwes et al. |
| 6,643,537 B1 | 11/2003 | Zatezalo et al. |
| 6,648,017 B2 | 11/2003 | Lamas et al. |
| 6,652,489 B2 | 11/2003 | Trocki et al. |
| 6,656,157 B1 | 12/2003 | Duchon et al. |
| 6,669,679 B1 | 12/2003 | Savage et al. |
| 6,676,104 B2 | 1/2004 | Tillander |
| 6,682,044 B2 | 1/2004 | Miller |
| 6,708,944 B2 | 3/2004 | Pfeil et al. |
| 6,731,971 B2 | 5/2004 | Evans, III et al. |
| 6,746,427 B2 | 6/2004 | Duchon et al. |
| 6,749,090 B2 | 6/2004 | Bailey |
| 6,752,789 B2 | 6/2004 | Duchon et al. |
| 6,857,617 B2 | 2/2005 | Forberg |
| 6,866,039 B1 | 3/2005 | Wright et al. |
| 6,866,654 B2 | 3/2005 | Callan et al. |
| 6,871,660 B2 | 3/2005 | Hampsch |
| 6,880,808 B2 | 4/2005 | McPeak et al. |
| 6,889,074 B2 | 5/2005 | Uber, III et al. |
| 6,892,996 B2 | 5/2005 | Starchevich |
| 6,901,283 B2 | 5/2005 | Evans, III et al. |
| 6,918,893 B2 | 7/2005 | Houde et al. |
| 6,929,235 B1 | 8/2005 | Height et al. |
| 6,929,236 B1 | 8/2005 | Height et al. |
| 6,929,619 B2 | 8/2005 | Fago et al. |
| 6,945,959 B2 | 9/2005 | Duchon et al. |
| 6,953,450 B2 | 10/2005 | Baldwin et al. |
| 6,953,453 B2 | 10/2005 | Recinella et al. |
| 6,958,053 B1 | 10/2005 | Reilly |
| 6,986,753 B2 | 1/2006 | Bui |
| 7,018,363 B2 | 3/2006 | Cowan et al. |
| 7,047,058 B1 | 5/2006 | Dvorsky et al. |
| 7,060,049 B2 | 6/2006 | Trombley, III et al. |
| 7,094,216 B2 | 8/2006 | Trombley, III et al. |
| 7,153,288 B2 | 12/2006 | Duchon et al. |
| 7,192,416 B1 | 3/2007 | Lazzaro et al. |
| 7,267,667 B2 | 9/2007 | Houde et al. |
| 7,553,294 B2 | 6/2009 | Lazzaro et al. |
| 7,556,619 B2 | 7/2009 | Spohn et al. |
| 7,566,320 B2 | 7/2009 | Duchon et al. |
| 7,662,124 B2 | 2/2010 | Duchon et al. |
| 7,666,169 B2 | 2/2010 | Cowan et al. |
| D618,334 S | 6/2010 | Le et al. |
| 7,766,883 B2 | 8/2010 | Rellly et al. |
| 7,879,008 B2 | 2/2011 | Haury et al. |
| 2002/0088954 A1 | 7/2002 | Miller |
| 2002/0130283 A1 | 9/2002 | Starchevich |
| 2002/0143294 A1 | 10/2002 | Duchon et al. |
| 2002/0183616 A1 | 12/2002 | Toews et al. |
| 2003/0071233 A1 | 4/2003 | Stewart et al. |
| 2003/0139706 A1 | 7/2003 | Gray |
| 2004/0064041 A1 | 4/2004 | Lazzaro et al. |
| 2004/0092885 A1 | 5/2004 | Duchon et al. |
| 2004/0122369 A1 | 6/2004 | Schriver et al. |
| 2004/0122370 A1 | 6/2004 | Joyce et al. |
| 2004/0158205 A1 | 8/2004 | Savage |
| 2004/0241023 A1 | 12/2004 | Pinkerton et al. |
| 2004/0254333 A1 | 12/2004 | Smits et al. |
| 2005/0104444 A1 | 5/2005 | Callan et al. |
| 2005/0113754 A1 | 5/2005 | Cowan |
| 2005/0230575 A1 | 10/2005 | Zelenski et al. |
| 2005/0234407 A1 | 10/2005 | Spohn et al. |
| 2005/0234428 A1 | 10/2005 | Spohn et al. |
| 2005/0245883 A1 | 11/2005 | Baldwin |
| 2005/0273056 A1 | 12/2005 | Haury et al. |
| 2006/0108008 A1 | 5/2006 | Guala |
| 2006/0155248 A1 | 7/2006 | Hashimoto et al. |
| 2006/0167415 A1 | 7/2006 | Nemoto |
| 2006/0178632 A1 | 8/2006 | Trombley et al. |
| 2006/0180202 A1 | 8/2006 | Wilson et al. |
| 2006/0184124 A1 | 8/2006 | Cowan et al. |
| 2007/0060874 A1 | 3/2007 | Nesbitt et al. |
| 2007/0204612 A1 | 9/2007 | Klimowicz |
| 2009/0112164 A1 | 4/2009 | Reilly et al. |
| 2010/0114040 A1 | 5/2010 | Schriver et al. |

FOREIGN PATENT DOCUMENTS

| | | |
|---|---|---|
| GB | 2108852 A | 5/1983 |
| WO | 9632975 A1 | 10/1996 |
| WO | 9707841 A2 | 3/1997 |
| WO | 0010629 A1 | 3/2000 |
| WO | 0152921 A2 | 7/2001 |
| WO | 0204049 A1 | 1/2002 |
| WO | 03015851 A1 | 2/2003 |

* cited by examiner

FIG.5A
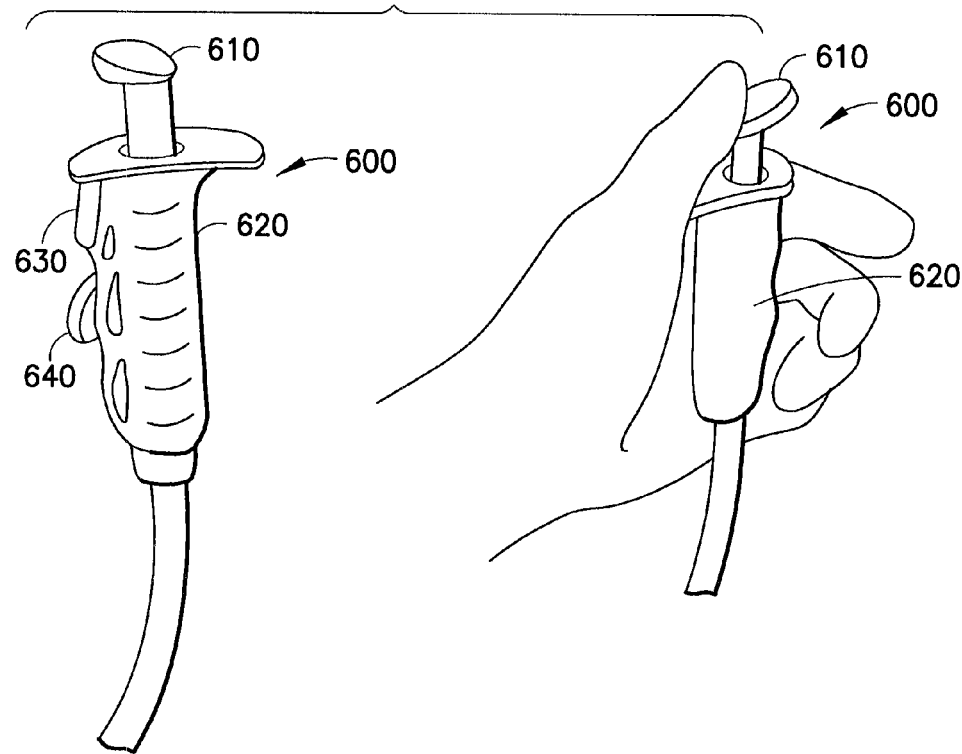
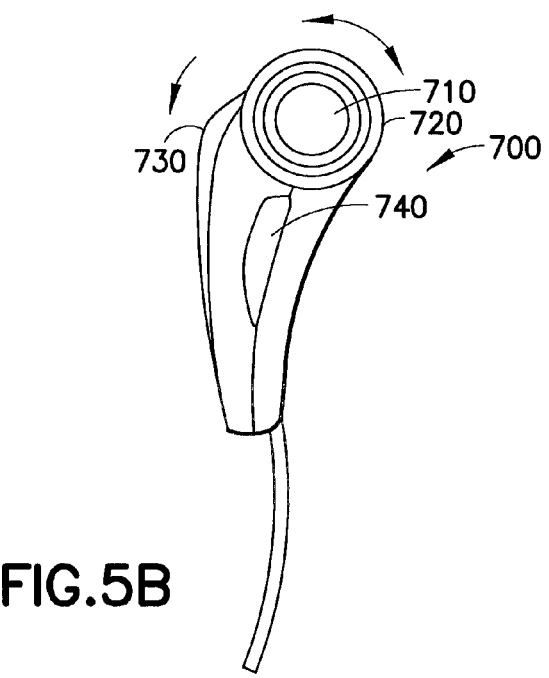
FIG.5B

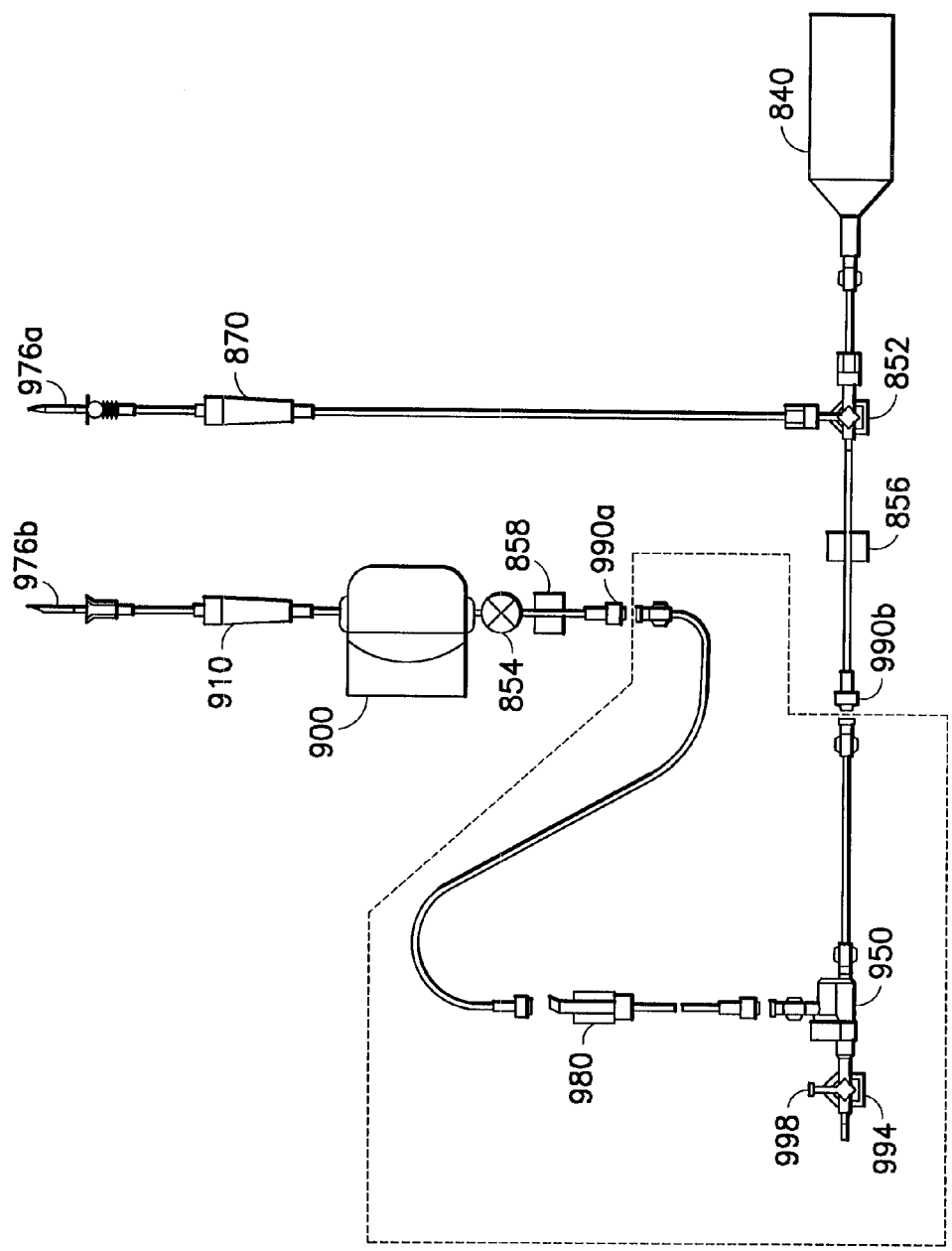

FLUID PATH CONTAINING A PRESSURE ISOLATION VALVE

CROSS REFERENCE TO RELATED APPLICATIONS

This application is a divisional application of U.S. application Ser. No. 11/238,666, filed on Sep. 29, 2005, now U.S. Pat. No. 8,747,358, issued Jun. 10, 2014, which is a divisional application of application Ser. No. 09/982,518, filed on Oct. 18, 2001, now U.S. Pat. No. 7,094,216, issued Aug. 22, 2006, which claims the benefit of Provisional Application Ser. No. 60/241,505, filed on Oct. 18, 2000, the disclosures of which are incorporated herein by reference.

BACKGROUND OF THE INVENTION

The present invention relates to powered injector systems and methods for use thereof in medical injection or fluid delivery procedures and, more particularly, to control of powered injector systems and methods of controlling powered injector systems.

In many medical diagnostic and therapeutic procedures, a physician or other person injects a patient with a fluid. In recent years, a number of injector-actuated syringes and powered injectors for pressurized injection of fluids such as contrast media have been developed for use in, procedures such as angiography, computed tomography, ultrasound and NMR/MRI. In general, these powered injectors are designed to deliver a preset amount of contrast media at a preset flow rate.

Angiography is used generally in the detection and treatment of abnormalities or restrictions in blood vessels. In an angiographic procedure, one obtains a radiographic image of vascular structure with the assistance of a radiographic contrast medium (sometimes referred to simply as contrast) injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a monitor and recorded.

In a typical angiographic procedure, a physician places a cardiac catheter into a vein or artery. The catheter is connected to either a manual or an automatic contrast injection mechanism. A typical manual contrast injection mechanism includes a syringe and a catheter connection. The operator of such a syringe adjusts the flow rate and volume of injection by altering the force applied to the plunger of the syringe. Manual sources of fluid pressure and flow used in medical applications such as syringes and manifolds thus typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters into an electronic control system of the powered injector a fixed volume of contrast material and a fixed rate of injection. In many systems, there is no interactive control between the operator and the powered injector, except to start or stop the injection. A change in flow rate in such systems occurs by stopping the machine and resetting the parameters. Automation of angiographic procedures using powered injectors is discussed, for example, in U.S. Pat. Nos. 5,460,609, 5,573,515 and 5,800,397.

U.S. Pat. No. 5,800,397 discloses an angiographic injector system having both high pressure and low pressure systems. The high pressure system includes a motor-driven injector pump to deliver radiographic contrast material under high pressure to a catheter. The low pressure system includes, among other things, a pressure transducer to measure blood pressure and a pump to deliver a saline solution to the patient as well as to aspirate waste fluid. A manifold is connected to the syringe pump, the low pressure system, and the patient catheter. A flow valve associated with the manifold is normally maintained in a first state connecting the low pressure system to the catheter through the manifold (and disconnecting the high pressure system from the catheter and the low pressure system). When pressure from the syringe pump reaches a predetermined and set level, the valve switches to a second state connecting the high pressure system/syringe pump to the catheter, while disconnecting the low pressure system from the catheter (and from the high pressure system). In this manner, the pressure transducer is protected from high pressures. See Col 3, lines 20-37. However, compliance in the system components (for example, expansion of the syringe, tubing and other components under pressure) using such a manifold system can lead to a less than optimal injection bolus. Moreover, the arrangement of the system components of U.S. Pat. No. 5,800,397 results in relatively large amounts of wasted contrast and/or undesirable injection of an excessive amount of contrast when the low pressure (saline) system is used.

The injector system of U.S. Pat. No. 5,800,397 also includes a handheld remote control connected to a console. The control includes saline push button switches and a flow rate control lever or trigger. By progressive squeezing of the control trigger, the user provides a command signal to the console to provide a continuously variable injection rate corresponding to the degree of depression of the control trigger.

Similarly, U.S. Pat. No. 5,916,165 discloses a handheld pneumatic controller for producing a variable control signal to control a rate of fluid disbursement to the patient in an angiographic system. U.S. Pat. No. 5,515,851 discloses an angiographic system with a finger activated control pad to regulate the injection of fluids.

Unlike manual injection systems, however, there is little if any feedback to the operator of system pressure in the above systems. There are potential advantages to such feedback. In the use of a manual syringe, for example, excessive backpressure on the syringe plunger can provide evidence of occlusion of the fluid path.

U.S. Pat. No. 5,840,026 discloses, among other things, an injection system in which an electronic control system is connected to the contrast delivery system and a tactile feedback control unit. In one embodiment, the tactile feedback control unit includes a disposable syringe that is located within a durable/reusable cradle and is in fluid connection with the fluid being delivered to the patient. The cradle is electrically connected to the electronic control system and is physically connected to a sliding potentiometer that is driven by the plunger of a disposable syringe.

During use of the injection system of U.S. Pat. No. 5,840,026, the doctor holds the cradle and syringe and, as the doctor depresses the sliding potentiometer/syringe piston assembly, the plunger is moved forward, displacing fluid toward the patient and creating a pressure in the syringe. A sliding potentiometer tracks the position of the syringe plunger.

The electronic control system controls the contrast delivery system to inject an amount of fluid into the patient based on the change in position of the plunger. As the fluid is injected, the pressure the doctor feels in his hand is proportional to the actual pressure produced by the contrast delivery system. The force required to move the piston provides the operator with tactile feedback on the pressure in the system. The doctor is able to use this feedback to ensure the safety of the injection procedure.

Unlike the case of a manual injection system, the injection system of U.S. Pat. No. 5,840,026 does not require the doctor to develop the system pressure and flow rate. The doctor develops a smaller, manually applied pressure, which corresponds to or is proportional to the system pressure. The required manual power output (that is, pressure×flow rate) is decreased as compared to manual systems, whereas the tactile feedback associated therewith is retained.

Although advances have been made in the area of angiographic injection systems, it remains desirable to develop injectors, injector systems and methods to facilitate such procedures.

SUMMARY OF THE INVENTION

The present invention provides an injector system including a powered injector, a pressurizing chamber in operative connection with the powered injector, a fluid path in fluid connection with the pressurizing chamber, and a manual control in fluid connection with the fluid path. The manual control includes at least one actuator for controlling the injector through application of force by an operator. The actuator provides tactile feedback of pressure in the fluid path to the operator via direct or indirect operative or fluid connection with the fluid path (that is, pressure in the fluid path transfers a corresponding or a proportional force to the operator). In one embodiment, the actuator is adapted to stop an injection procedure if no force is applied to the actuator. The manual control can, for example, include a chamber in fluid connection with the fluid path. The actuator can be a button or a plunger in operative connection with a piston disposed within the chamber. The actuator can be biased in an off position.

In another aspect, the manual control includes a first actuator for controlling the injector in a low-pressure mode through application of force by an operator. The first actuator provides tactile feedback of pressure in the fluid path to the operator via fluid connection with the fluid path as described above. The first actuator also provides control of flow rate by changing the force thereon. The manual control also can include a second actuator having an on state and an off state. The second actuator causes the injector to enter into a preprogrammed high-pressure injection mode when placed in the on state. The manual control can also include a third actuator for controlling flow of saline in the fluid path.

In another aspect of the present invention, the actuator provides tactile feedback of fluid pressure and is also in operative connection with an audible feedback unit that provides audible feedback of fluid pressure and/or fluid flow to the operator. The manual controls of the present invention can be purged of air before injection via, for example, a purge valve.

The present invention also provides a system for injection of fluid into a patient including a multi-patient reusable section and a per-patient disposable section. The multi-patient reusable section and the per-patient disposable section are removably connectable via a connector or connectors (for example, via a high-pressure connector). The multi-patient reusable section includes a powered injector in fluid connection with a source of a first injection fluid and a first fluid path connecting the injector and a high-pressure connector. The per-patient disposable section includes a second fluid path adapted to connect the high-pressure connector and the patient in fluid connection. The per-patient disposable section further includes a manual control as described above including a connector to place the manual control in fluid connection with the second fluid path. The multi-patient reusable section can further include a valve mechanism connecting the injector, first fluid source and the first fluid path.

In one embodiment, the multi-patient reusable section further includes a source of a second injection fluid and a pumping mechanism in fluid connection with the second fluid source for pressurizing the second fluid. The pumping mechanism is preferably in fluid connection with the valve mechanism.

In one aspect, the manual control includes a first actuator providing control of flow rate of the first fluid by changing the force on the first actuator and a second actuator, the second actuator causing the injector to enter into a preprogrammed high pressure injection mode when placed in an on state. The system can further include a pressure sensor in fluid communication with the second fluid path via a pressure-activated isolator that isolates the pressure sensor from pressures in the second fluid path above a set pressure. In one embodiment, the per-patient disposable section can include a check valve in the second fluid path separating components of the per-patient disposable section from the multi-patient reusable section to reduce or eliminate flow of contaminated fluid into the multi-patient reusable section.

The present invention further provides a method of injecting a fluid into a patient including the steps of: removably connecting a multi-patient reusable section to a per-patient disposable section via a high-pressure connector, the multi-patient reusable section including a powered injector in fluid connection with a source of a first injection fluid and a first fluid path connecting the injector and the high-pressure connector, the per-patient disposable section including a second fluid path adapted to connect the high-pressure connector and the patient in fluid connection; connecting a manual control including a connector to the second fluid path to place the manual control in fluid connection with the second fluid path, the manual control including at least one actuator for controlling the powered injector through application of force by an operator, the actuator being adapted to provide tactile feedback of pressure in the second fluid path to the operator via fluid connection with the second fluid path; and injecting a fluid into a patient.

The method can further include the step of connecting a pressure sensor in fluid communication with the second fluid path via a pressure activated isolator that isolates the pressure sensor from pressures in the second fluid path above a set pressure.

Still further, the present invention provides a per-patient disposable set for use in an injection procedure including a fluid path adapted to form a fluid connection between a high-pressure connector and the patient, and a manual control in fluid connection with the fluid path. The manual control includes at least one actuator for controlling the powered injector through application of force by an operator. The actuator is adapted to provide tactile feedback of pressure in the fluid path to the operator via fluid connection with the fluid path. The per-patient disposable set further includes a pressure sensor in fluid connection with the fluid path via a pressure activated isolator adapted to isolate the pressure sensor from pressures in the fluid path above a set pressure.

The manual (for example, handheld) controllers of the present invention provide a number of advantages including, but not limited to the following: tactile feedback of actual fluid path pressure via fluid communication with the fluid path, compact size and small priming volume; dead man switch capability; ergonomic design for control of both contrast and saline; injection pressure feedback linked to variable flow and audible feedback; rigid material construction; actuator control providing a progressively increasing flow rate as the actuator is pushed or depressed through its range of motion; and high-pressure injections that are greater in pressure than could be tolerated by an operator's hand.

In another aspect, the present invention provides an injection system for use in angiography including a powered injector in fluid connection with a source of injection fluid and a pressure sensor in fluid connection with the powered injector via a pressure activated isolator adapted to isolate the pressure sensor from pressures in the fluid path above a set pressure. The pressure sensor elevation is independent of or independently variable of the position of the remainder of the injection system, including the position or elevation of the powered injector.

In a further aspect, the present invention provides an angiographic injection system for injecting an injection fluid into a patient including a pressurizing device for supplying injection fluid under pressure; a low pressure fluid delivery system; and a pressure isolation mechanism having a first port for connection to the pressurizing device, a second port for connection to the patient, and a third port for connection to the low pressure fluid delivery system. The pressure isolation mechanism includes a valve having a first state and a second state different from the first state. Preferably, the first state and the second state are mutually exclusive of each other. The first state occurs when the second and third ports are connected and the first and third ports are connected. The second state occurs when the first and second ports are connected and the first and third ports are disconnected. The valve is normally biased to the first state (via, for example, a spring) and is switchable to the second state when fluid pressure from the syringe pump reaches a predetermined pressure level. The first and second ports remain connected in the first state and in the second state.

The system preferably further includes a valve in line between the pressurizing device and the first port of the pressure isolation mechanism to control flow of the injection fluid. Preferably, the valve is an automated valve. The valve is preferably operable to minimize or eliminate the effects of compliance of the pressurizing device and related tubing.

The low pressure delivery system can include a source of saline or other suitable flushing medium, a drip chamber in fluid connection with the source of saline and a detector to sense the amount of saline in the source of saline. The system can further include a saline control valve and an air detector in line between the saline drip chamber and the pressure isolation mechanism.

The pressurizing device can be in fluid connection with a source of injection fluid via an injection fluid drip chamber. The system can further include a detector to sense the amount of injection fluid in the source of injection fluid. Likewise, the system can also include an injection fluid control valve and an air detector in line between the injection fluid drip chamber and the pressure isolation mechanism.

In one embodiment, the system further includes a handheld controller to control injection of injection fluid and injection of saline. The handheld controller can include a first control having a first mode to control injection of injection fluid in a low pressure mode, the flow rate of the injection corresponding to (for example, being proportional to) the distance the first control is depressed. Preferably, the low pressure injection is ceased if the first control is released while in the first mode. The first control can, for example, have a second mode to control injection of injection fluid in a high pressure mode. The high pressure mode injection is preferably ceased if the first control is released while in the second mode. The hand controller can further include at least a second control to control injection of saline. Preferably, the injection of saline is ceased if the second control is released during injection of saline.

The system preferably further includes a pressure transducer in fluid connection with the third port of the pressure isolation mechanism.

In still a further aspect, the present invention provides an injection system for use in angiography including a source of saline, a pump in fluid connection with the source of saline to pressurize the saline, a saline valve in fluid connection via a first port thereof with an outlet of the pump, a first connector in fluid connection with a second port of the saline valve, a source of contrast, a contrast valve in fluid connection with the source of contrast via a first port of the contrast valve, a powered injector in fluid connection with a second port of the contrast valve, a second connector in fluid connection with a third port of the contrast valve, and a pressure isolation mechanism.

The pressure isolation mechanism has a lumen having a first port in fluid connection with the second connector and a second port in fluid connection with a patient catheter. The isolation mechanism further has a third port in fluid connection with the first connector and with the lumen. The pressure isolation mechanism further includes a valve having a first state and a preferably mutually exclusive second state—the first state occurring when the lumen and the third port are connected, and the second state occurring when the lumen and the third port are disconnected. The valve is preferably normally biased to the first state and is switchable to the second state when fluid pressure from the powered injector reaches a predetermined pressure level. The first and second ports of the lumen preferably remain connected whether in the first state or in the second state. The system further includes a pressure transducer in fluid connection with the third port of the pressure isolation mechanism.

The system can also include a first air or air column detector in fluid connection between the saline valve and the first connector and a second air detector in fluid connection between the contrast valve and the second connector.

The system can also include a first drip chamber in fluid connection between the source of saline and the pump and a detector in operative connection with the first drip chamber to sense the amount of saline in the source of saline. Likewise, the system can include a second drip chamber in fluid connection between the source of contrast and the contrast valve and a detector in operative connection with the second drip chamber to sense the amount of injection fluid in the source of injection fluid. One advantage of a drip chamber is to reduce likelihood of introduction of air into the system once the system has been initially purged or air or primed.

Numerous other objects and advantages of the present invention will be apparent from the following drawings and detailed description of the invention and its preferred embodiments.

BRIEF DESCRIPTION OF THE DRAWINGS

FIG. 5A illustrates another embodiment of a handheld controller of the present invention including a control switch for pressure feedback in low pressure injection, a switch for high pressure injection and a switch for saline injection.

FIG. 5B illustrates another embodiment of a handheld controller of the present invention, which is wearable on a finger of the user.

FIG. 6B illustrates a side view of an embodiment of a portion of the injection system of FIG. 6A in which a pressure transducer is in the fluid path.

DETAILED DESCRIPTION OF THE INVENTION

In one aspect, the present invention provides an energy/signal source to generate fluid pressure/flow while also providing user tactile and/or audible feedback of the fluid pressure generated, allowing the user to modulate the fluid pressure/flow. The powered injection system of the present invention is capable of providing, for example, both precise low-flow/low-pressure fluid delivery for powered coronary injections and high-flow/high-pressure fluid delivery for ventricle injections.

Figure 1:
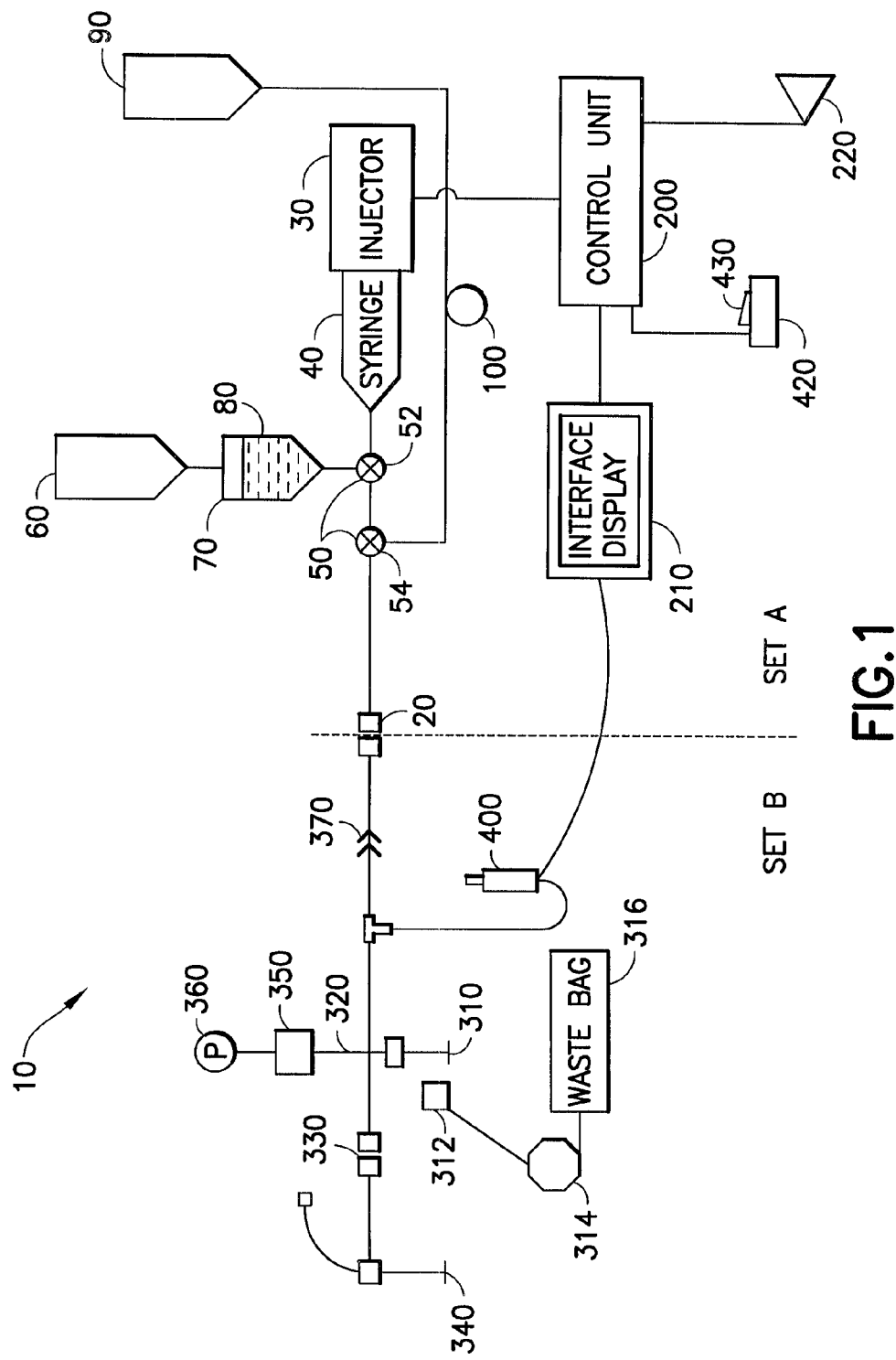
FIG. 1 illustrates one embodiment of an injection system of the present invention.

FIG. 1 illustrates one embodiment of the present invention in which injection system 10 is preferably divided into two sections: A) a multi-patient section or B) set and a per-patient disposable section or set. Section or set A and section or set B are preferably separated and removably coupled into fluid connection by a high-pressure connector or by a high-pressure, "aseptic" connector 20 such as the septum connector disclosed in U.S. Pat. No. 6,096,011, assigned to the assignee of the present invention, the disclosure of which is incorporated herein by reference. The aseptic coupler or connector of U.S. Pat. No. 6,096,011 is suitable for repeated use (coupling and uncoupling) at relatively high pressures. Aseptic connector 20 preferably maintains a leakproof seal at high pressures after many such uses and can, for example, include a surface that can be disinfected (for example, between patients) by wiping with a suitable disinfectant. Another high-pressure aseptic connector suitable for use in the present invention is disclosed in U.S. patent application Ser. No. 09/553,822, filed on Apr. 21, 2000, assigned to the assignee of the present invention, the disclosure of which is incorporated herein by reference.

Multi-patient set A preferably includes a powered injector 30 which is typically an electromechanical drive system for generating fluid pressure/flow via, for example, a pressurizing chamber such as syringe 40 as known in the art. Suitable powered injectors and syringes for use in the present invention are disclosed, for example, in PCT Publication No. WO 97/07841 and U.S. Pat. No. 4,677,980, assigned to the assignee of the present invention, the disclosures of which are incorporated herein by reference.

In general, the injector drive is an electromechanical device that creates linear motion acting on a syringe plunger (not shown in FIG. 1) to provide the generation of fluid pressure/flow. A source of injection media 60 (for example, a contrast bottle) is in fluid connection with the syringe via, for example, an electromechanical valve assembly 50 for controlling and directing fluid flow by acting upon preferably disposable valves 52 and 54. Valves 52 and 54 are preferably multi-position valves that are fluid wetted. Valves 52 and 54 can alternatively or additionally be manually operated. Contrast bottle or container 60 can be prepackaged contrast media, often distributed in a glass or plastic container with a rubber septum for allowing connections via IV spikes. An interim container or reservoir 70 is preferably placed between contrast bottle 60 and electromechanical valve assembly 50 to provide an air gap in the fluid path to enable purging of air from the system and to allow level detection of contrast source 60. Interim reservoir 70 can operate in conjunction with a contrast level detection system as described in further detail below. A contrast level detector 80 can, for example, include one or more electrical, optical, ultrasound, or mechanical sensors that detect the presence of fluid at a certain level in interim reservoir 70.

Further protection against injection of air into a patient can be provided by variety of mechanisms for detection of air in the fluid path or stream. For example, ultrasonic bubble detection can be used to detect the presence of air in the fluid path. Likewise, backlighting can be used for bubble detection. In the backlighting method of bubble detection, the injector side of the fluid path is illuminated to increase visualization of the fluid path, fluid presence and air presence.

At least one source 90 of another fluid (typically saline or other suitable medium) can also be provided. Additional fluid sources, such as therapeutic fluids, can also be provided. Additional fluid sources such as saline supply 90 are preferably in operative or fluid connection with a pressurizing mechanism such as a powered injector or a peristaltic pump 100. In FIG. 1, peristaltic pump 100 in operative connection with the saline source 90 is in fluid connection with the fluid path of injector 30 via electromechanical valve assembly 50.

A controller unit 200 provides power to injector 30 and to peristaltic pump 100 in a controlled manner. Controller unit 200 provides communication between the various system components. A graphical user interface display 210 is preferably provided in connection with controller unit 200 to display information to the user and to enable the user to set and adjust device parameters. An audible feedback source 220 can be provided, for example, to provide feedback to the user of the rate of flow provided by injector 30. For example, a sound can increase in pitch, volume and/or frequency as flow rate is increased.

Per-patient disposable set B includes fluid wetted components of the fluid delivery path. Per-patient disposable set B preferably includes a waste port 310 (for example, through which patient blood can be drawn), a pressure measurement port 320, and an interface 330 to a catheter 340 (for example, a connector such as a standard Luer connector). Waste port 310 can, for example, include a manually activated or automated valve to allow discharge of unwanted fluid and connection of, for example, manually operated syringes. Moreover, a powered aspiration mechanism (for example, a peristaltic pump 314 connected via tubing to a waste bag 316) can be connected to waste port 310 via, for example, a standard connector 312, to aspirate fluid from the system as well as to draw blood from the patient. Drawing fluid from the system and blood from the patient into waste bag 316 assists in eliminating air from the fluid delivery system.

Figure 2:
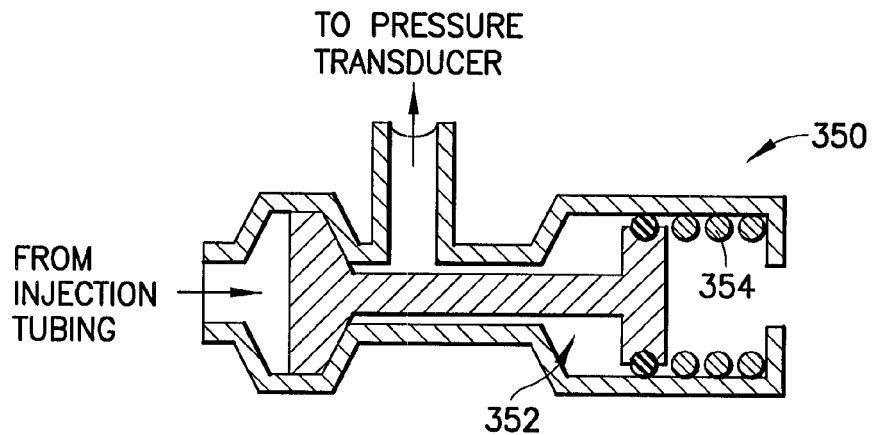
FIG. 2 illustrates an embodiment of a pressure activated isolator assembly of the present invention.

Pressure port 320 preferably includes a pressure-activated isolator 350 for pressure transducer isolation as, for example, illustrated in FIG. 2. Pressure-activated isolator 350 is a fluid activated assembly that is located in line with the injection flow. In the embodiment of FIG. 2, a valve 352 within the assembly isolates pressure transducer 360 by shutting off during high-pressure injections. A spring 354 returns valve 352 to its original open position when the injector system is not injecting at high pressure, thus opening the fluid path to pressure transducer 360. In the embodiment of FIGS. 1 and 2, pressure-activated isolator 350 transitions to a closed position to isolate only pressure transducer 360, which is not in fluid connection with contrast source 60 or saline source 90 other than through pressure-activated isolator 350. Pressure transducer 360 can, for example, be located near the patient to substantially reduce or remove pressure signal dampening resulting from intervening tubing, fluid and system components and thereby improve accuracy as compared to other pressure measurement systems currently used in angiographic procedures. Preferably, pressure transducer 360 is separated by a minimum (for example, by no more than approximately three feet) of tubing from the patient/catheter connector. Because of the multi-patient nature of set A, the pressure transducer assembly and the remainder of per-patient disposable set B are preferably located downstream of a double check valve 370 to provide continuous measurements. As such, a pressure isolation mechanism such as described above is required to isolate pressure transducer 360 from high pressure during power injection.

Figure 3:
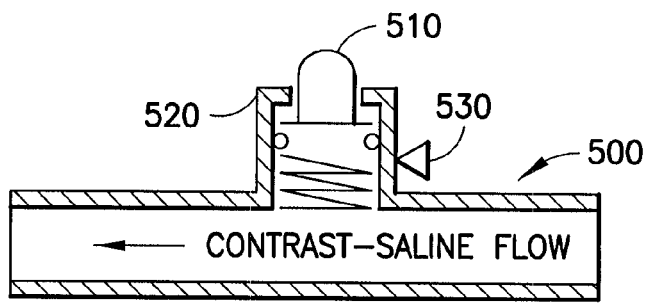
FIG. 3 illustrates an embodiment of a handheld controller or hand piece of the present invention.
Figure 4:
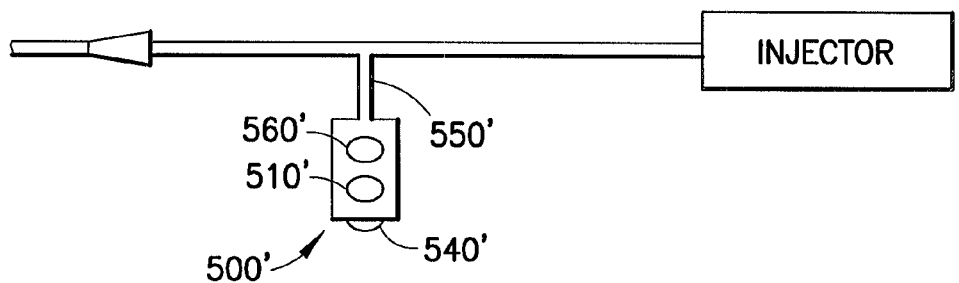
FIG. 4 illustrates another embodiment of a handheld controller of the present invention in which the handheld controller is connected to the fluid path via a "T" connection.

The system also includes a manually operated, for example, a handheld or hand operated, control 400 that can, for example, generate or process a control signal that is electrical, mechanical, pneumatic, optical, radio frequency, audible or any combination thereof to effect control of injector 30 and preferably to also effect control of peristaltic pump 100. Handheld control 400 also preferably provides feedback (for example, tactile, visual, audible etc.) of the injected fluid pressure and flow to the operator. Handheld control 400 preferably provides at least tactile feedback. In the embodiments of FIGS. 1, 3 and 4, the handheld control or hand piece is in operative communication with the fluid flow and allows the user to feel the pressure in the fluid path line. Preferably, an electrical switch allows the user to turn on/off and modulate the fluid/flow pressure of the system for low-pressure/low-flow coronary injections only. High-pressure injection is activated, for example, using either display 210 or a separate (second) control on the handheld control. The handheld control thus provides pressure feedback to the user while controlling the injection.

The handheld controls of the present invention can, for example, include a fluid path containment chamber in which a movable element is able to travel a pre-determined distance. The moveable element is preferably in direct contact with the fluid path and is affected by fluid flow and pressure. The movable element incorporates a mechanism to process a signal, which can be used to control the fluid pressure/flow source remotely. The handheld device is capable of being used with a signal processor related to the movement of the moveable element as known in the art.

In one embodiment of the present invention, a handheld control device 500 incorporates a moveable piston 510 slideably disposed within a chamber 520 in a direction generally perpendicular to the direction of fluid flow as illustrated in FIG. 3. Chamber 520 and piston 510 can be directly in the fluid path or can be spaced from the fluid path by a length of tubing (see, for example, FIG. 4). Handheld device 500 allows moveable piston 510 to be positioned under one finger while device 500 is held in the hand. Piston 510 preferably incorporates a switch 530 that, when compressed, controls the fluid flow generated by an external fluid pressure/flow source (for example, injector 30). Upon generation of the pressure, piston 510 is displaced by increased pressure, which is detectable by the operator. Further compression of piston 510 by the operator preferably increases the signal to the fluid flow/pressure generator, resulting in an increase in the pressure/flow and an increased pressure on piston 510, which is felt by the operator. Backpressure or tubing occlusion causes increased pressure in the system, upward movement of piston 510 and tactile feedback to the operator, thereby alerting the operator to potential problems in the injection procedure. The system can also provide audible and/or visual feedback of the flow rate via, for example, user display 210 that is preferably controlled by the position of piston 510.

As illustrated in FIG. 4, a handheld control 500' can be connected in a "T" 550 off of the main line for more flexibility. A purge valve 540 can be located at the end of handheld control 500' for air elimination during system purge. Air can also be purged from the handheld control 500' before it is connected to the fluid path. FIG. 4 also illustrates a second switch 560' for initiation of a high pressure injection. An additional switch or switches can also be provided to, for example, control delivery of saline.

FIGS. 5A and 5B illustrate other, ergonomic handheld controls. Handheld control 600 of FIG. 5A includes a chamber 620 that can be in fluid connection with the injection system fluid path as described above. A low pressure control switch 610 similar in operation to piston 510 is slideably disposed within chamber 620 to control low-pressure injections of contrast. Chamber 620 can, for example, be formed to conform to the hand of the user. A switch 630 to begin a high pressure injection via injector 30 is provided on handheld control 600. Also, a switch 640 to control delivery of saline is provided on handheld control 600.

FIG. 5B illustrates an embodiment of a finger-wearable handheld control 700. In that regard, a finger of the user's hand passes through passage 710 in control 700 while control 700 is held in the user's hand. A rotating switch 720 controls low-pressure injection. A high pressure injection switch 730 and a saline switch 740 are also provided.

System 10 can also include a manually operated foot controller 420 including one or more actuators 430 in communication with controller 200. Foot controller 420 can, for example, be used to control flow through system 10 in conjunction with or independently of handheld controller 400.

Another embodiment of an injector system 800 is illustrated in FIGS. 6A through 6H. In this embodiment (referring primarily to FIGS. 6A and 6G), a fluid control module 810 is in operative connection with a powered injector 830 to which a syringe 840 is connected as described above. Syringe 840 is in fluid connection with an automated valve 852 of fluid control module 810, which is also in fluid connection with a source of contrast 860 via an intermediate drip chamber 870. Drip chamber 870 preferably includes a fluid level sensing mechanism 880. A preferably automated valve/stopcock 852 such as known in the art is also in fluid connection with a first, inlet port of a lumen 954 of a pressure isolation valve 950. Valve 852 prevents saline and/or contaminated fluids from entering syringe 840 and enables the operator to stop flow of injection fluid (for example, contrast) from syringe 840 quickly at any pressure or flow rate. This ability to substantially immediately stop flow of injection fluid at any pressure and flow rate substantially removes the effects of system compliance and enables delivery of a "sharp" bolus. An air column detector 856 can be placed in line between stopcock 852 and pressure isolation valve 950.

Fluid control module 810 further includes a source of saline 890 in fluid connection with a peristaltic pump 900 via an intervening drip chamber 910. Drip chamber 910 preferably includes a fluid level sensing mechanism 920. Peristaltic pump 900 is in fluid connection with a preferably automated valve/stopcock 854, which is in fluid connection with pressure isolation valve 950. In addition to controlling flow of saline, valve 854 prevents contaminated fluids from reaching peristaltic pump 900 and saline source 890. An air column detector 858 can be placed in line between stopcock 854 and pressure isolation valve 950.

A controller 970 and a display 974 (see FIG. 6A) are also in operative connection with injector 830 as described above. Furthermore, handheld controller 1000 is in operative connection with injector 830 and thereby with fluid control module 810. In the embodiment of FIGS. 6A through 6H, handheld controller 1000 does not provide tactile feedback of system pressure to the operator. However, a handheld controller providing such tactile feedback (for example, handheld controller 600) can readily be used in connection with system 800. Moreover, a foot controller as described above can also be provided.

In general, the preferably per-patient disposable portion or set of system 800 is illustrated within dashed lines in FIGS. 6A, 6B, 6C and 6G. Two connectors 990a and 990b (which are preferably aseptic connectors as described above) are used to connect the multi-patient fluid path set with the per-patient fluid path set. Use of two separate/parallel fluid lines and two separate connectors to connect the multi-patient set with the per-patient disposable set affords a number of benefits over current angiographic injection systems including decrease contrast wastage and avoidance of injecting potentially hazardous amounts of contrast into the patient during saline purges. Moreover, system 800 facilitates close placement of pressure transducer 980 to the patient, improving measurement accuracy as compared to currently available systems. Although handheld controller 1000 in the embodiments of FIGS. 6A through 6H is not in direct connection with the fluid path, it is preferably disposable because of contamination with bodily fluids that typically occurs from operator handling thereof.

Lumen 954 (via a second, outlet port thereof) of pressure isolation valve 950 is preferably in fluid connection with an automated or manual valve/stopcock 994, which preferably includes a waste port 996 as described above. Catheter 1100 is preferably connected via a rotating Luer connection 998.

Figure 6A:
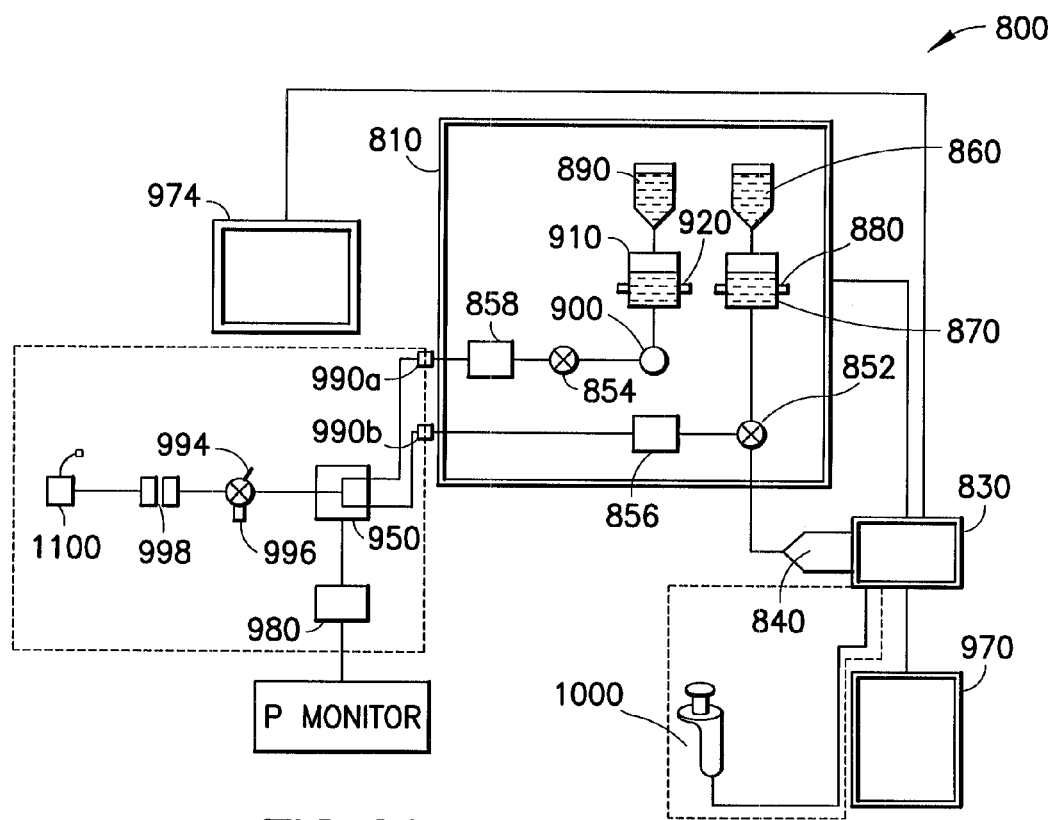
FIG. 6A illustrates a schematic representation of another embodiment of an injection system of the present invention.
Figure 6C:
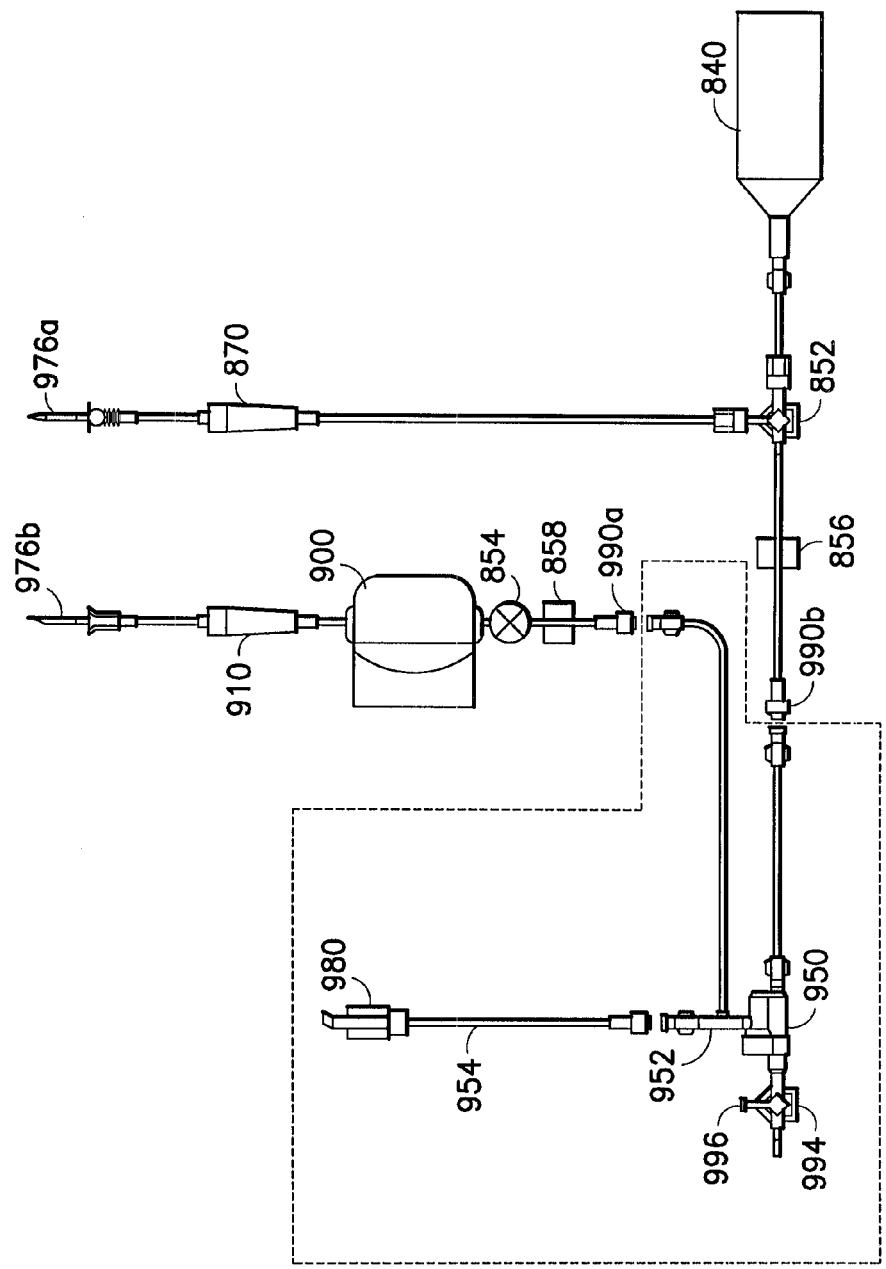
FIG. 6C illustrates a side view of an embodiment of a portion of the injection system of FIG. 6A in which a pressure transducer is separated from the fluid path by a T-connector and a length of tubing.

FIG. 6B illustrates a portion of a fluid path set for use in system 800 of FIG. 6A in which a pressure transducer 980 is directly in the saline fluid path. FIG. 6C illustrates a fluid path set for use in system 800 of FIG. 6A in which pressure transducer 980 is separated from the saline fluid path by a "T" connector 952 and a length of tubing 954. In the embodiments of FIGS. 6B and 6C, spikes 976a and 976b are used to connect to contrast source 860 and saline source 890, respectively. In general, standard Luer connections are used to connect most of the components of system 800. In FIGS. 6B and 6C several of these Luer connections are illustrated in a disconnected state. Alternatively, one or more of the illustrated connections can, for example, be non-Luer or bonded connections.

Figure 6F:
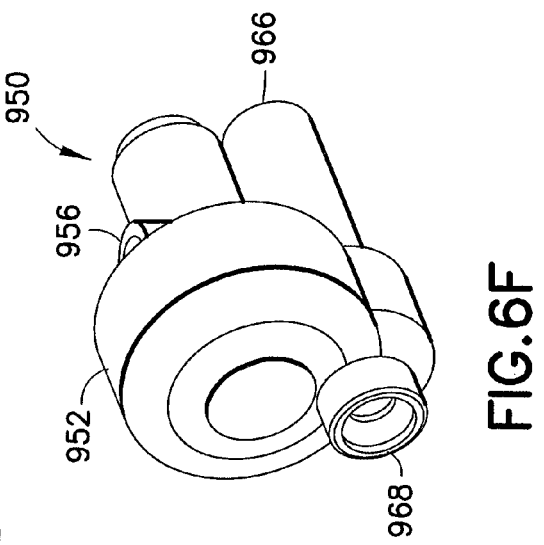
FIG. 6F illustrates a perspective view of the pressure isolation valve of FIGS. 6D and 6E.
Figure 6D:
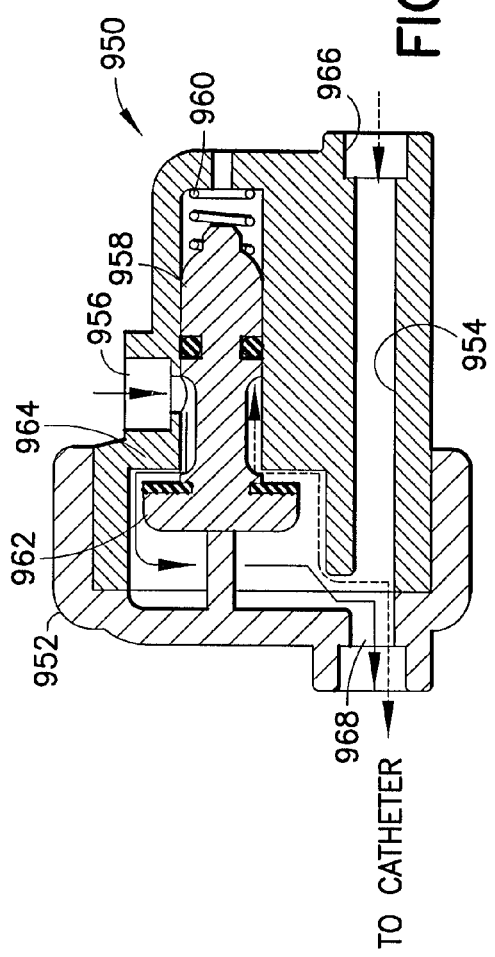
FIG. 6D illustrates a side cross-sectional view of an embodiment of a pressure isolation valve of the present invention in which the valve is in a first, "open" state.
Figure 6E:
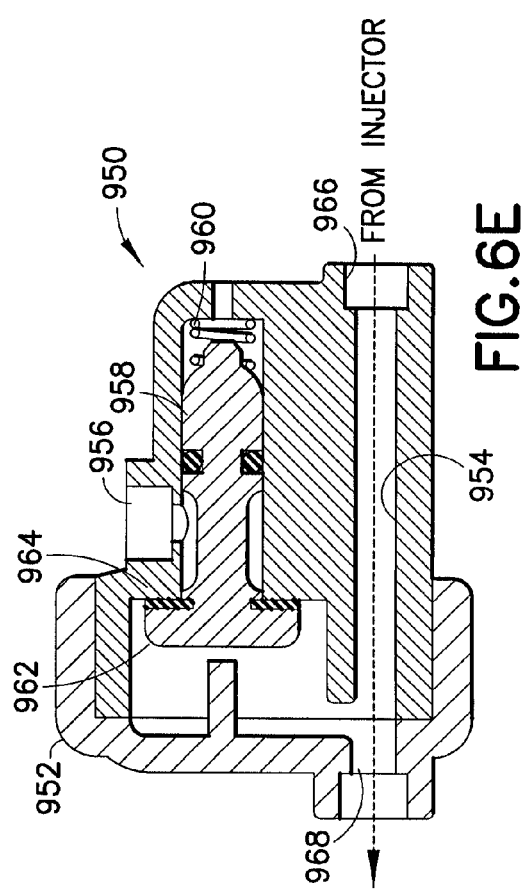
FIG. 6E illustrates a side cross-sectional view of the pressure isolation valve of FIG. 6D in which the valve is in a second, "closed" state.

One embodiment of a pressure isolation valve 950 is illustrated in FIGS. 6D through 6F. Pressure isolation valve 950 includes a housing 952 with a high pressure lumen 954, through which fluid passes under pressure. Pressure isolation valve 950 also includes a port 956 to which pressure transducer 980 and saline source 890 are connected. A piston 958 acts to isolate pressure transducer 980 once a given pressure is reached in lumen 954 of pressure isolation valve 950. In an "open" or rest state, as shown in FIG. 6D, there is hydraulic or fluid communication between lumen 954 (including catheter 1100 and syringe 840 connected thereto), and isolation port 956 (including pressure transducer 980 and the saline fluid path connected thereto).

Preferably, the clearances and apertures within pressure isolation valve 950 are sufficiently generous to transmit changes in pressure that normally occur during normal heart function quickly, as to not damp the signal. The pressure effect on piston 958 of the flow of injection fluid from syringe 840 through lumen 954 is illustrated with dashed arrows in FIG. 6D while the flow of saline through pressure isolation mechanism 950 is illustrated with solid arrows. When the pressure within lumen 954 increases during an injection, piston 958 responds by moving to the right in the orientation of FIGS. 6D and 6E, compressing a spring 960 until a seal portion 962 at the left end of piston 958 contacts a sealing seat 964 as illustrated in FIG. 6E. At this point, lumen or port 956 is isolated from lumen 954 and any additional increase in pressure acts to increase or improve the effectiveness of the seal 962. When the pressure within lumen 954 subsides, spring 960 reopens pressure isolation valve 950 by pushing piston 958 to the left. In one embodiment, fluid does not flow through port 956. In this embodiment, pressure isolation valve 950 only isolates the tubing and devices distal to port 956 from high pressure and does not control flow.

As discussed above, saline is used occasionally during routine catheterization procedures. For example, controls 1030a or 1030b on handheld control 1000 can send a signal to control the flow of saline. For patient safety, it is desirable to introduce the saline close to the proximal end of catheter 1100 so the amount of contrast purged ahead of the saline is minimized during a saline injection. Once again, the parallel line configuration of the contrast delivery and saline deliver fluid paths of present invention assist in preventing such undesirable injections.

Since the required saline flow rates are low and the viscosity of saline is much lower than the viscosity of contrast, the pressures required to force saline through catheter 1100 are much less than that of contrast. By protecting the saline line from the high pressures required for contrast injection, additional system compliance is avoided and the saline line does not need to be made of the same high-pressure line as the contrast. Protection of the saline line from high pressure is accomplished by connecting the saline line to port 956 of pressure isolation valve 950 to introduce the saline flow as illustrated with solid arrows in FIG. 6D. In this embodiment, port 956 is normally open, permitting the flow of saline therethrough, when required, as well as the monitoring of the patient blood pressure. During a high-pressure injection, pressure isolation valve 950 functions as described above and protects pressure transducer 980 and the low-pressure saline line from the high contrast injection pressures.

The elevation of catheter 1100 often changes during the course of an injection procedure, for example, as the patient is raised or lowered. Such changes in elevation of catheter 1100 can result in erroneous blood pressure readings by pressure transducer 980. Therefore, pressure transducer 980 is preferably positioned such that it changes elevation with catheter 1100 and is not dependent upon the position of the injection system, including the position of injector 830.

Figure 6G:
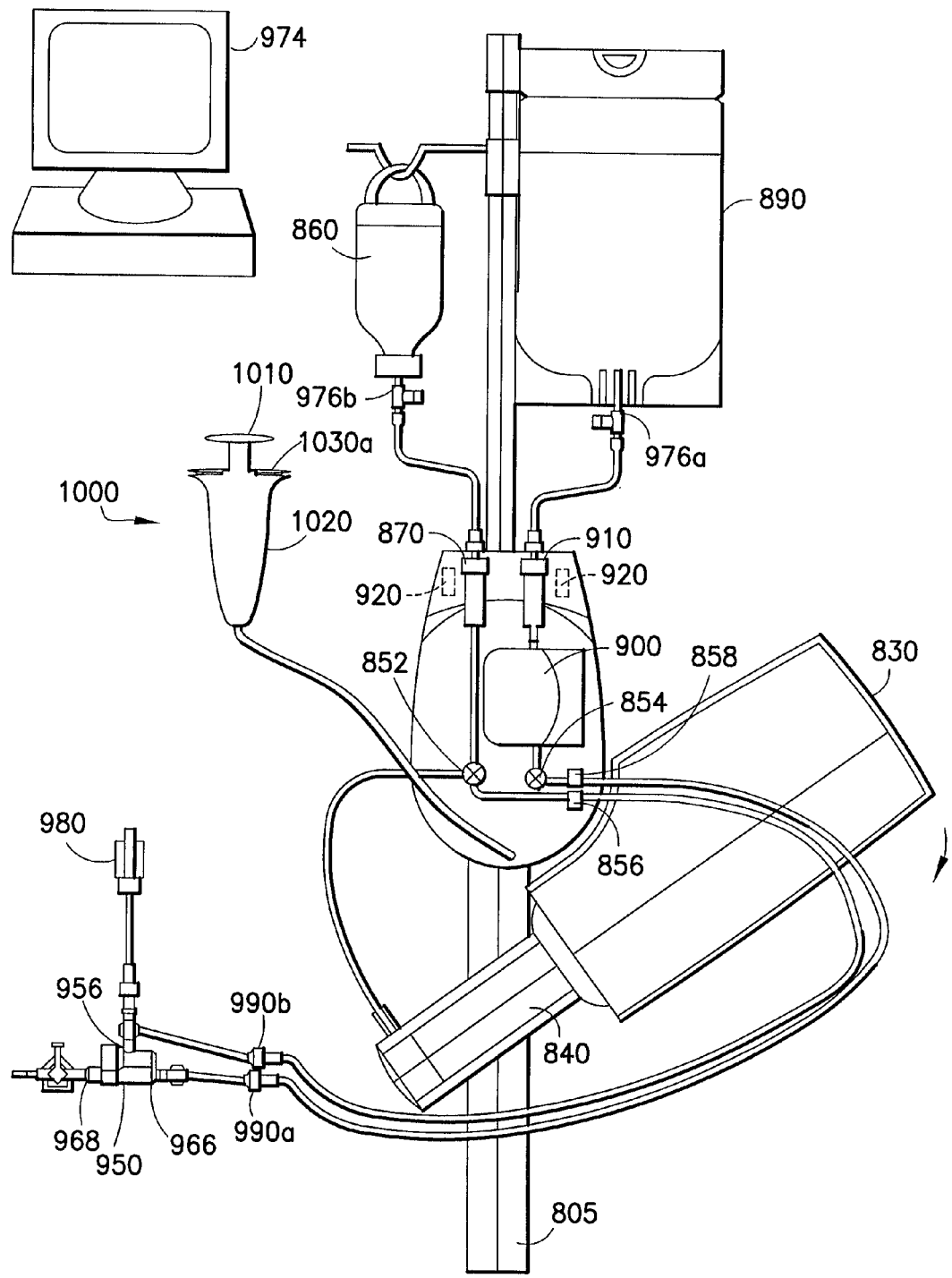
FIG. 6G illustrates a front view of the injection system of FIG. 6A.
Figure 6H:
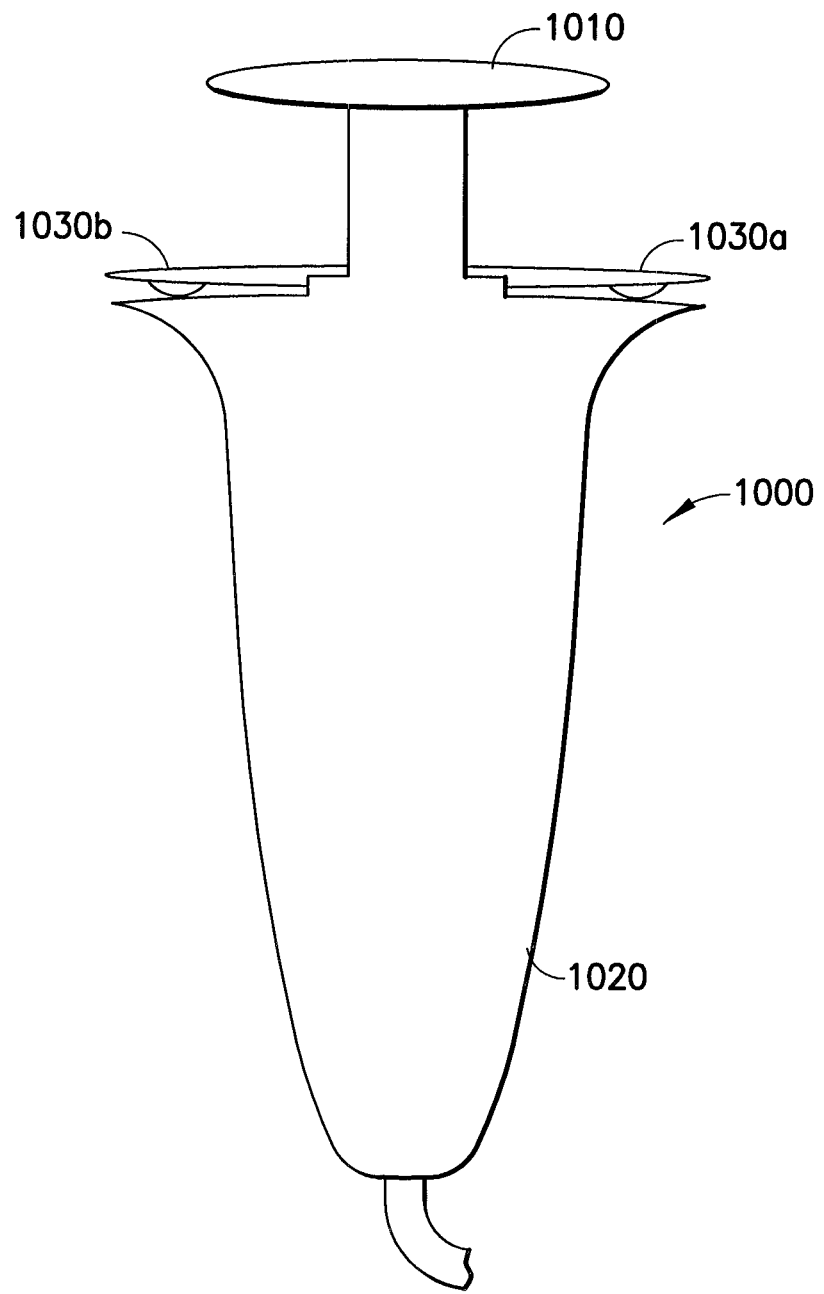
FIG. 6H illustrates a front view of the handheld controller of the injection system of FIG. 6A.

In one embodiment in FIGS. 6G and 6H, handheld controller 1000 included a plunger or stem control 1010 that, when in a first/low pressure mode, is depressed by the operator to control the flow of contrast from syringe 840. The farther plunger 1010 is depressed, the greater the flow rate (via, for example, a potentiometer such as a linear potentiometer within housing 1020 of controller 1000). In this embodiment, the operator can use graphical user interface display 974 to change the mode of plunger 1010 to a second mode in which it causes injector 830 to initiate a high pressure injection as preprogrammed by the operator. In this second/high pressure mode, the operator maintains plunger 1010 in a depressed state to continue the injection. Preferably, if plunger 1010 is released, the high-pressure injection is terminated substantially immediately, for example, by control of valve 852. Handheld controller 1000 also includes at least one switch to control saline flow in system 800. In the embodiment of FIG. 6H, handheld controller 1000 includes two saline switches 1030a and 1030b on either side of plunger 1010 for ease of access by the operator. In this embodiment, switches 1030a and 1030b include resilient cantilevered members 1032a and 1032b, respectively, which are depressed by the operator to deliver saline through system 800. Preferably, one of switches 1030a or 1030b must be maintained in a depressed state by the operator to continue delivery of saline. If the depressed switch is release, saline flow is preferably stopped substantially immediately, for example, via control of valve 854.

As illustrated in FIG. 6G, many of the components of system 800 can be supported on a mobile stand 805. Injector 830 is preferably rotatable about stand 805 as indicated by the arrow of FIG. 6G. In one embodiment of system 800 of FIGS. 6G and 6H: stopcocks were obtained from Medical Associates Network, Inc., a distributor for Elcam Plastic, under product number 565302; spikes were obtained from Qosina under product numbers 23202 and 23207, tubing was obtained from Merit Medical under product numbers DCT-100 and DCT-148; connectors were obtained from Merit Medical under product number 102101003, a rotating hub was obtained from Medical Associates Network, Inc., a distributor for Elcam Plastic, under product number 565310; a peristaltic, pump from Watson-Marlow was obtained having a product number of 133.4451.THF; and fluid level sensors from Omron were obtained under product number EESPX613.

The following describes a typical use scenario of injection systems of the present invention and assumes that all fluid path components are assembled/connected and located in their proper position, including contrast and saline containers.

Typically, the first step in an injection procedure is replacing air in the fluid path with fluid. By operator initiation and machine control, the powered injector causes the syringe plunger to move rearward (toward the powered injector), thereby creating a negative pressure at the connection point to a control valve in proximity to the contrast interim container. The control valve is positioned to allow fluid flow from the contrast bottle, into the interim container and into the syringe. Upon drawing a predetermined amount of contrast into the syringe, the injector drive preferably reverses direction creating a positive pressure and fluid movement in the direction of the contrast container or the catheter (which is not connected to a patient) to drive any entrapped air out of the fluid path into an "air gap" established in the interim container or through the catheter. Air is further preferably initially purged from the system during start-up by, for example, distributing a fluid such as saline through the fluid path (sometimes referred to as "priming"). The system is preferably maintained air-free during an injection procedure and with multi-patient use. Priming is preferably done once per patient or once per multi-patient, depending on disposable fluid path configuration.

The system can include, for example, "contrast low" level (need for refill) and "stop filling" limit sensors on the interim reservoir as described above to help ensure that air is not aspirated into the contrast syringe during a fill cycle. An ultrasonic air column sensor or sensors and/or other types of sensors can also be included downstream of the injector to detect air gaps within the line as a secondary safety sensor.

By operator initiation and machine control, a second fluid pump connected to a bulk source of saline, typically a prefilled bag, provides fluid flow in the direction of patient catheter. Enough saline is preferably pumped throughout disposable set to achieve elimination of all visible air during priming. Using the saline priming feature, a handheld controller that is in fluid connection with the fluid path (to provide tactile feedback as described above) can, for example, be purged of air by opening an integral bleed valve. After priming is complete the bleed valve is closed.

Once the system is properly set up and primed, it can be connected to the patient via the catheter. The system preferably has a range of parameters for flow, pressure, variable flow, alarms and performance limits as known in the art.

To deliver contrast at low flow and low pressure, for example, to the coronary arteries, depressing a first button, piston or other controller on the handheld controller initiates flow of contrast and in some embodiments provides feedback (for example, tactile and/or audible feedback). Further depressing the button on the hand controller preferably increases the flow rate of contras. If at any time the button is released, the fluid flow preferably stops and any feedback ends. This "dead-man" operability can be provided, for example, by biasing (for example, spring loading) the first control or actuator toward the off position. The minimum and maximum flow are preferably established by the parameters set using a graphical user interface on the display.

To deliver contrast at high flow and high pressure, for example, to the left ventricle, a separate switch or second actuator/controller on the hand control is preferably depressed. Alternatively, a second mode of the first actuator/controller can be entered to control high pressure flow. In embodiments in which the handheld control provides tactile feedback during low-pressure injection, preferably no such tactile feedback is provided during high pressure flow. However, other feedback such as an audible tone feedback different than any audible tone provided during the low-pressure mode can be provided. The high-pressure/high-flow function is preferably first input/selected from the parameters input/set using the graphical user interface on the display. The high-flow and high-pressure injection is preferably preprogrammed and the flow cannot be varied. As discussed above, any direct, tactile feedback is preferably eliminated, as the pressure is often over 1000 psi. If at any time the second button is released, the injection preferably stops.

To deliver saline, a second or third switch, controller or actuator on the hand controller is preferably selected, causing saline flow at a pre-selected flow rate. Alternatively, a single controller or actuator having three different control modes can be used. As with the other actuators or actuator modes on the handheld controller, if at any time the third button is released, the saline flow preferably stops.

A pressure sensor is preferably connected to a pressure isolation valve as described above. Patient pressure monitoring can be determined at any time except when an injection of fluid exceeds the pressure set by the pressure isolation valve.

A multi-patient set can be designed so that at least some portions thereof can safely be reused for multiple patients. In such a design, for example, the syringe and interface to contrast/saline components, disposable valves and related tubing, and a multi-use high-pressure, aseptic connector can preferably be reused for multiple patients.

Handheld controllers (whether or not in fluid connection with the fluid path) and related tubing and check valves are preferably replaced for each patient. Likewise, any waste port, pressure port, and the interface to catheter are preferably replaced for each patient. Aseptic connectors of a multi-patient set can, for example, be wiped clean before connecting a disposable se for each new patient. Reusable or multi-patient sets preferably have a limited numbers of reuses and preferably are not used for longer than a set period of time (for example, an 8-hour period).

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations that come within the meaning and range of equivalency of the claims are to be embraced within their scope.

The invention claimed is:

1. A fluid path set for use in a fluid delivery system, comprising:
a multi-patient use section adapted for connection to a pump device and to a source of injection fluid; and
a per-patient use section adapted for removable fluid communication with the multi-patient use section, the per-patient use section comprising a pressure isolation mechanism, wherein the pressure isolation mechanism comprises: a first port adapted for connection to the pump device via the multi-patient use section, a second port adapted for connection to a patient, a pressure isolation port adapted for connection to a source of medical fluid via the multi-patient use section, a lumen connecting the first port and the second port, and a valve member biased to a normally open position permitting fluid communication between the first port, the second port, and the pressure isolation port, and movable to a closed position to close the pressure isolation port when fluid pressure in the lumen reaches a predetermined pressure level sufficient to overcome a biasing force applied to the valve member.

2. The fluid path set of claim 1, wherein the multi-patient use section further comprises a multi-position valve adapted to selectively isolate the pump device, the source of the injection fluid, and the per-patient use section.

3. The fluid path set of claim 1, further comprising a pressure transducer associated with the pressure isolation port.

4. The fluid path set of claim 1, wherein the multi-patient use section further comprises an intervening drip chamber between the source of medical fluid and the pressure isolation port.

5. The fluid path set of claim 1, wherein the multi-patient use section is connectable to the per-patient use section by a pair of connectors.

6. The fluid path set of claim 1, wherein the lumen is in fluid communication with an automated or a manual valve having a waste port.

7. The fluid path set of claim 1, further comprising a spike for connecting the multi-patient use section with the source of the injection fluid.

8. The fluid path set of claim 1, wherein the valve member comprises a spring that applies the biasing force to maintain the valve member in the normally open position.

9. The fluid path set of claim 1, wherein the valve member comprises a sealing portion for sealing the pressure isolation port when the valve member is in the closed position.

10. The fluid path set of claim 9, further comprising a sealing seat that contacts the sealing portion of the valve member when the valve member is in the closed position.

11. The fluid path set of claim 1, wherein the valve member is linearly movable between the normally open position and the closed position.

12. The fluid path set of claim 1, wherein, in the normally open position, the pressure isolation mechanism is configured for permitting fluid flow through the lumen and permitting monitoring of a blood pressure of the patient.

13. A pressure isolation mechanism, comprising:
a housing defining a lumen with a first port, a second port, and a pressure isolation port; and
a valve member disposed within the housing, the valve member biased to a normally open position permitting fluid communication between the first port, the second port, and the pressure isolation port, and movable to a closed position to close the pressure isolation port when fluid pressure in the lumen reaches a predetermined pressure level sufficient to overcome a biasing force applied to the valve member.

14. The pressure isolation mechanism of claim 13, further comprising a pressure transducer associated with the pressure isolation port.

15. The pressure isolation mechanism of claim 13, wherein the lumen is in fluid communication with an automated or a manual valve having a waste port.

16. The pressure isolation mechanism of claim 13, wherein the valve member comprises a spring that applies the biasing force to maintain the valve member in the normally open position.

17. The pressure isolation mechanism of claim 13, wherein the valve member comprises a sealing portion for sealing the pressure isolation port when the valve member is in the closed position.

18. The pressure isolation mechanism of claim 17, wherein the housing comprises a sealing seat that contacts the sealing portion of the valve member when the valve member is in the closed position.

19. The pressure isolation mechanism of claim 13, wherein the valve member is linearly movable between the normally open position and the closed position.

20. The pressure isolation mechanism of claim 13, wherein, in the normally open position, the pressure isolation mechanism is configured for permitting fluid flow through the lumen and permitting monitoring of a patient's blood pressure.

* * * * *